(12) United States Patent
Govari

(10) Patent No.: US 7,397,364 B2
(45) Date of Patent: Jul. 8, 2008

(54) DIGITAL WIRELESS POSITION SENSOR

(75) Inventor: Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 390 days.

(21) Appl. No.: 10/706,298

(22) Filed: Nov. 11, 2003

(65) Prior Publication Data

US 2005/0099290 A1    May 12, 2005

(51) Int. Cl.
   *G08B 1/08* (2006.01)
   *H04Q 7/00* (2006.01)
   *A61B 19/00* (2006.01)
   *A61B 5/05* (2006.01)
   *A61B 6/00* (2006.01)
   *G08B 21/00* (2006.01)

(52) U.S. Cl. .............. 340/539.12; 340/539.1; 340/539.22; 340/657; 340/825.72; 340/825.73; 600/424; 600/430; 600/431; 606/130

(58) Field of Classification Search ........ 340/870, 340/539.12, 539.22, 657, 825.72, 825.73; 600/424, 301; 607/32, 60
See application file for complete search history.

(56) References Cited

U.S. PATENT DOCUMENTS

| | | | |
|---|---|---|---|
| 4,173,228 A | 11/1979 | Van Steenwyk et al. |
| 4,905,698 A | 3/1990 | Strohl, Jr. et al. |
| 5,099,845 A | 3/1992 | Besz et al. |
| 5,325,873 A | 7/1994 | Hirschi et al. |
| 5,329,944 A | 7/1994 | Fabian et al. |
| 5,391,199 A | 2/1995 | Ben-Haim |
| 5,425,367 A | 6/1995 | Shapiro et al. |
| 5,425,382 A | 6/1995 | Golden et al. |
| 5,443,489 A | 8/1995 | Ben-Haim |
| 5,558,091 A | 9/1996 | Acker et al. |
| 5,913,820 A | 6/1999 | Bladen et al. |
| 6,172,499 B1 | 1/2001 | Ashe |
| 6,198,963 B1 | 3/2001 | Haim et al. |
| 6,239,724 B1 | 5/2001 | Doron et al. |
| 6,261,247 B1 | 7/2001 | Ishikawa et al. |

(Continued)

FOREIGN PATENT DOCUMENTS

EP    0776176    12/1999

(Continued)

*Primary Examiner*—Brian L. Casler
*Assistant Examiner*—Parikha S Mehta
(74) *Attorney, Agent, or Firm*—Ladas and Parry LLP

(57) ABSTRACT

A method is provided for tracking an object, including positioning a radio frequency (RF) driver to radiate an RF driving field toward the object, and fixing to the object a wireless transponder that includes a power coil and at least one sensor coil. The method also includes receiving the RF driving field using the power coil and storing electrical energy derived therefrom. A plurality of field generators are driven to generate electromagnetic fields at respective frequencies in a vicinity of the object that induce a voltage drop across the at least one sensor coil. A digital output signal is generated at the wireless transponder indicative of the voltage drop across the sensor coil, and the generation of the digital output signal is powered using the stored electrical energy. The digital output signal is transmitted from the wireless transponder using the power coil, and the transmission of the digital output signal is powered using the stored electrical energy. The digital output signal is received and processed to determine coordinates of the object.

31 Claims, 4 Drawing Sheets

U.S. PATENT DOCUMENTS

| | | | |
|---|---|---|---|
| 6,369,564 B1 | 4/2002 | Khalfin et al. | |
| 2003/0120150 A1* | 6/2003 | Govari | 600/424 |
| 2006/0267759 A1* | 11/2006 | Levine | 340/539.12 |

FOREIGN PATENT DOCUMENTS

| | | |
|---|---|---|
| EP | 1321097 | 6/2003 |
| WO | 96/05768 | 2/1996 |
| WO | 00/16686 | 3/2000 |
| WO | 01/12108 | 2/2001 |

\* cited by examiner

DIGITAL WIRELESS POSITION SENSOR

FIELD OF THE INVENTION

The present invention relates generally to intrabody tracking systems, and specifically to wireless methods and devices for tracking the position and orientation of an object in the body.

BACKGROUND OF THE INVENTION

Many surgical, diagnostic, therapeutic and prophylactic medical procedures require the placement of objects such as sensors, treatment units, tubes, catheters, implants and other devices within the body. These procedures cover a large spectrum including, for example:

insertion of electrodes for therapeutic or diagnostic purposes, placement of tubes to facilitate the infusion of drugs, nutritional and other fluids into a patient's circulatory system or digestive system, insertion of probes or surgical devices to facilitate cardiac or other types of surgery, and biopsies or other diagnostic procedures.

In many instances, insertion of a device is for a limited time, such as during surgery or catheterization. In other cases, devices such as feeding tubes or orthopedic implants are inserted for long-term use. The need exists for providing real-time information for accurately determining the location and orientation of objects within the patient's body, typically without using X-ray imaging.

U.S. Pat. Nos. 5,391,199 and 5,443,489 to Ben-Haim, whose disclosures are incorporated herein by reference, describe systems wherein the coordinates of an intrabody probe are determined using one or more field sensors, such as a Hall effect device, coils, or other antennae carried on the probe. Such systems are used for generating three-dimensional location information regarding a medical probe or catheter. Preferably, a sensor coil is placed in the catheter and generates signals in response to externally-applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

U.S. Pat. No. 6,198,963 to Ben-Haim et al., whose disclosure is incorporated herein by reference, describes simplified apparatus for confirmation of intrabody tube location that can be operated by nonprofessionals. The initial location of the object is determined as a reference point, and subsequent measurements are made to determine whether the object has remained in its initial position. Measurements are based upon one or more signals transmitted to and/or from a sensor fixed to the body of the object whose location is being determined. The signal could be ultrasound waves, ultraviolet waves, radio frequency (RF) waves, or static or rotating electromagnetic fields.

European Patent EP 0 776 176 and corresponding PCT Publication WO 96/05768 to Ben-Haim et al., whose disclosures are incorporated herein by reference, describe a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates.

U.S. Pat. No. 5,558,091 to Acker et al., whose disclosure is incorporated herein by reference, describes a magnetic position and orientation determining system which uses uniform fields from Helmholtz coils positioned on opposite sides of a sensing volume and gradient fields generated by the same coils. By monitoring field components detected at a probe during application of these fields, the position and orientation of the probe is deduced. A representation of the probe is superposed on a separately-acquired image of the subject to show the position and orientation of the probe with respect to the subject.

U.S. patent application Ser. No. 10/029,473 to Govari published as U.S. Patent Application Publication 2003/0120150, and is assigned to the assignee of the present patent application and incorporated herein by reference. Apparatus for tracking an object is described, including a plurality of field generators, which generate electromagnetic fields at different, respective frequencies in a vicinity of the object, and a radio frequency (RF) driver, which radiates an RF driving field toward the object. A wireless transponder is fixed to the object. The transponder includes at least one sensor coil, in which a signal current flows responsive to the electromagnetic fields, and a power coil, which receives the RF driving field and conveys electrical energy from the driving field to power the transponder. The power coil also transmits an output signal responsive to the signal current to a signal receiver, which processes the signal to determine coordinates of the object.

U.S. Pat. No. 6,239,724 to Doron et al., whose disclosure is incorporated herein by reference, describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

U.S. Pat. No. 6,172,499 to Ashe, whose disclosure is incorporated herein by reference, describes a device for measuring the location and orientation in the six degrees of freedom of a receiving antenna with respect to a transmitting antenna utilizing multiple-frequency AC magnetic signals. The transmitting component consists of two or more transmitting antennae of known location and orientation relative to one another. The transmitting antennae are driven simultaneously by AC excitation, with each antenna occupying one or more unique positions in the frequency spectrum. The receiving antennae measure the transmitted AC magnetic field plus distortions caused by conductive metals. A computer then extracts the distortion component and removes it from the received signals, providing the correct position and orientation output.

U.S. Pat. No. 4,173,228 to Van Steenwyck et al., whose disclosure is incorporated herein by reference, describes a catheter locating device based upon inducing a signal in a coil attached to the catheter and monitoring the amplitude and phase of the induced signal.

U.S. Pat. No. 5,099,845 to Besz et al., and U.S. Pat. No. 5,325,873 to Hirschi et al., whose disclosures are incorporated herein by reference, describe apparatus and methods in which a radiating element is fixed to a medical tube, e.g., a catheter, and the position of the tube is determined responsive to energy radiated from the element.

U.S. Pat. No. 5,425,382 to Golden, et al., whose disclosure is incorporated herein by reference, describes apparatus and methods for locating a medical tube in the body of a patient by sensing the static magnetic field strength gradient generated by a magnet fixed to the medical tube.

U.S. Pat. No. 4,905,698 to Strohl et al. and U.S. Pat. No. 5,425,367 to Shapiro, et al., whose disclosures are incorporated herein by reference, describe apparatus and methods wherein an applied magnetic field induces currents within a coil at the tip of a catheter. Based on these currents, the relative location of the catheter is determined.

U.S. Pat. No. 5,913,820 to Bladen et al., whose disclosure is incorporated herein by reference, describes apparatus for locating the position of a sensor, typically in three dimensions, by generating magnetic fields which are detected at the sensor. The magnetic fields are generated from a plurality of locations and enable both the orientation and location of a single coil sensor to be determined.

U.S. Pat. No. 6,369,564 to Khalfin et al., whose disclosure is incorporated herein by reference, describes an electromagnetic position and orientation tracking system with distortion compensation employing wireless sensors. The system uses one source of an AC electromagnetic field, at least one witness sensor measuring components of the electromagnetic induction vector at known spatial points close to or within the volume of interest, at least one wireless probe sensor placed on the object being tracked, and a control and processing unit which defines coordinates and attitude of the secondary source and, in turn, the position and orientation of the object of interest.

U.S. Pat. No. 6,261,247 to Ishikawa et al., whose disclosure is incorporated herein by reference, describes an anatomical position sensing system that uses one or more substantially spherical transponders for measuring relative positions and distances. Transponders are capable of receiving and transmitting RF signals, and communicating between themselves and with a separate CPU, which is controlled by an operator at an operator control panel.

PCT Patent Publication WO 01/12108 to Forsell et al., whose disclosure is incorporated herein by reference, describes a medical implant apparatus that receives energy wirelessly from a transmitter external to a patient's body. An implanted energy transforming apparatus transforms the energy so received into a different form, which different form is used in the control and operation of an implanted medical device.

PCT Patent Publication WO 00/16686 to Brockway et al., whose disclosure is incorporated herein by reference, describes a sensor device, such as a pressure monitor, which is implanted in the body of a patient, and which wirelessly communicates pressure information to a remote communication device. The sensor device can be implanted using a placement catheter, an endoscope, or a laparoscope. The wireless communication techniques include radio-telemetry, inductive coupling, passive transponders, and using the body as a conductor. In one embodiment, the sensor device receives energy wirelessly from a remote source, such as an energy source external to the body. This energy can be used to power the sensor device directly or to charge a rechargeable battery that powers the sensor device.

Commercial electrophysiological and physical mapping systems based on detecting the position of a probe inside the body are presently available. Among them, CARTO™, developed by Biosense Webster Inc. (Tirat HaCarmel, Israel), is a system for automatic association and mapping of local electrical activity with catheter location.

SUMMARY OF THE INVENTION

In embodiments of the present invention, apparatus for sensing the position and orientation of an object placed within a patient's body comprises a wireless location transponder containing a power coil, at least one sensing coil, and a signal processing chip module. Typically, the transponder is fixed to a device inserted into the body, such as a catheter or implant. The signal processing chip module typically comprises an arithmetical logic unit (ALU) and a power storage device, such as a capacitor. An externally-located driving unit sends a radio frequency (RF) signal, typically having a frequency in the megahertz range, to drive the power coil in the transponder and thereby charge the power storage device. A set of magnetic field generators in fixed locations outside the body then produce magnetic fields, typically at different, respective frequencies in the kilohertz range. These fields cause a time-varying voltage drop across the sensing coil, which depends on the spatial position and orientation of the sensing coil relative to the field generators. Using the energy stored in the power storage device, the ALU converts the phase and amplitude of the voltage into digital values, which are transmitted using a digital RF signal, typically in the megahertz range, to an externally-located signal processing unit. This unit processes the received digital signal to determine position and orientation coordinates of the object for display and recording.

In some embodiments of the present invention, the signal processing chip module further comprises a memory, in which the ALU stores the phase and amplitude digital values prior to their transmission. After these digital values are stored, the driving unit again charges the power storage device. The stored values are transmitted using this stored energy.

The techniques described herein enable the determination of the position and orientation of an object in the body without the need for any wired connection between the sensing coil and the external processing unit. Because the power transmission and digital signal transmission do not occur simultaneously, the techniques described herein typically prevent interference between the power transmission signal and the position signal. This lack of interference typically enhances the signal-to-noise ratio. Additionally, only a small amount of digital information is necessary to characterize the voltage generated across the sensing coil. As a result, the transponder requires low power to transmit this digital information, allowing for the use of a small power storage device, such as a capacitor, that can quickly be adequately charged. Furthermore, position coordinates are generally highly accurate because the information is transmitted digitally, and therefore is less susceptible to errors incurred from interference, distortion, or other phenomena sometimes associated with analog signal transmissions.

For some applications, the transponder comprises multiple sensor coils, typically three mutually-orthogonal coils. In this case, all six position and orientation coordinates can be determined without ambiguity, as described in the above-referenced European Patent EP 0 776 176.

There is therefore provided, in accordance with an embodiment of the present invention, a method for tracking an object, including:

positioning a radio frequency (RF) driver to radiate an RF driving field toward the object;

fixing to the object a wireless transponder including a power coil and at least one sensor coil;

receiving the RF driving field using the power coil and storing electrical energy derived therefrom;

driving a plurality of field generators to generate electromagnetic fields at respective frequencies in a vicinity of the object that induce a voltage drop across the at least one sensor coil;

generating a digital output signal at the wireless transponder indicative of the voltage drop across the sensor coil, and powering the generation of the digital output signal using the stored electrical energy;

transmitting the digital output signal from the wireless transponder using the power coil, and powering the transmission of the digital output signal using the stored electrical energy; and receiving and processing the digital output signal to determine coordinates of the object.

In an embodiment, driving the plurality of field generators includes driving the plurality of field generators to generate the electromagnetic fields at different respective frequencies, and the voltage drop across the at least one sensor coil has frequency components at the different respective frequencies of the plurality of field generators.

In an embodiment, the method includes inserting the transponder, together with the object, into a body of a subject. In this case, positioning the plurality of field generators and the RF driver typically includes placing the plurality of field generators and the RF driver outside the body.

In an embodiment, the method includes inserting the transponder, together with the object, into a body of a subject during a medical procedure, and removing the transponder from the body of the subject during the medical procedure.

For some applications, the object includes an elongate probe, for insertion into a body of a subject, and fixing the transponder to the object includes fixing the transponder in the probe. In this case, receiving and processing the digital output signal typically includes determining the coordinates of a distal end of the probe in the body.

In an embodiment, generating the digital output signal includes operating the transponder powered solely by the electrical energy derived from the RF driving field by the power coil.

For some applications, receiving the RF driving field includes receiving the RF driving field: (a) during a first time period, prior to driving the plurality of field generators, and (b) during a second time period, subsequent to the first time period and prior to transmitting the digital output signal. Storing the electrical energy derived from the RF driving field includes storing first electrical energy during the first time period and storing second electrical energy during the second time period. Powering the generation of the digital output signal includes powering the generation of the digital output signal using the first stored electrical energy. Powering the transmission of the digital output signal includes powering the generation of the digital output signal using the second stored electrical energy.

In an embodiment, receiving the RF driving field includes receiving the RF driving field during a time period prior to driving the plurality of field generators. Storing the electrical energy includes storing the electrical energy during the time period. Powering the generation of the digital output signal includes powering the generation of the digital output signal using the electrical energy stored during the time period. Powering the transmission of the digital output signal includes powering the transmission of the digital output signal using the electrical energy stored during the time period.

In an embodiment, generating the output signal includes:
measuring signal components of the voltage drop; and
converting the components into digital values.

In this case, measuring the signal components typically includes measuring an amplitude and a phase.

For some applications, the object includes an implant for implantation in a body of a subject. Fixing the transponder to the object includes fixing the transponder to the implant, and receiving and processing the digital output signal includes determining the coordinates of the implant within the body. For example, the implant may include a joint implant, including a first joint portion and a second joint portion that articulates therewith. In this case, fixing the transponder includes fixing a plurality of transponders respectively to the first joint portion and the second joint portion, and determining the coordinates of the implant includes determining a distance between the first joint portion and the second joint portion responsive to digital output signals from the transponders. Typically, but not necessarily, determining the distance includes finding the distance using the transponders during both intraoperative and post-operative periods.

There is further provided, in accordance with an embodiment of the present invention, a method for tracking an object, including:

radiating a radiofrequency (RF) driving field toward the object;

receiving the RF driving field at the object, and storing electrical energy derived therefrom;

subsequently to storing the electrical energy, generating a plurality of electromagnetic fields at respective frequencies in a vicinity of the object;

using the stored electrical energy, generating a digital output signal indicative of respective strengths of the electromagnetic fields at the object;

transmitting the digital output signal from the object; and
receiving and processing the digital output signal to determine coordinates of the object.

In an embodiment, generating the digital output signal includes generating the digital output signal solely using the stored electrical energy derived from the RF driving field.

There is still further provided, in accordance with an embodiment of the present invention, a method for tracking an object, including:

radiating a radiofrequency (RF) driving field toward the object;

receiving the RF driving field at the object, and storing electrical energy derived therefrom;

subsequently to storing the electrical energy, generating a plurality of electromagnetic fields at respective frequencies in a vicinity of the object;

using the stored electrical energy, generating an output signal indicative of respective strengths of the electromagnetic fields at the object;

transmitting the digital output signal from the object; and
receiving and processing the digital output signal to determine coordinates of the object.

In an embodiment, generating the output signal includes generating a digital output signal. Alternatively, generating the output signal includes generating an analog output signal.

There is yet further provided, in accordance with an embodiment of the present invention, apparatus for tracking an object, including:

(a) a radio frequency (RF) driver, adapted to radiate an RF driving field toward the object;

(b) a plurality of field generators, adapted to generate electromagnetic fields at respective frequencies in a vicinity of the object;

(c) a wireless digital transponder, fixed to the object, the transponder including:
  a power coil, coupled to receive the RF driving field;
  a power storage device, adapted to store electrical energy derived from the RF driving field;
  at least one sensor coil, coupled so that a voltage drop is induced across the at least one sensor coil responsive to the electromagnetic fields; and
  a control circuit, coupled to the at least one sensor coil and to the power storage device, and adapted to use the stored electrical energy to generate a digital output signal indicative of the voltage drop and adapted to use the stored electrical energy to drive the power coil to transmit the digital output signal; and
(d) a signal receiver, adapted to receive the digital output signal transmitted by the power coil and, responsive thereto, to determine coordinates of the object.

In an embodiment, the apparatus is configured such that:
the power storage device is adapted to store first electrical energy derived from the RF driving field during a first time period,
the control circuit is adapted to use the first stored electrical energy to generate the digital output signal,
the power storage device is adapted to store second electrical energy derived from the RF driving field during a second time period, following the first time period and following the generating by the control circuit of the digital output signal, and
the control circuit is adapted to use the second stored electrical energy to drive the power coil to transmit the digital output signal.

For some applications, the plurality of field generators are adapted to generate the electromagnetic fields at different respective frequencies.

In an embodiment, the control circuit is adapted to operate powered solely by the electrical energy conveyed thereto by the power coil.

In an embodiment, the voltage drop across the at least one sensor coil has frequency components at the different frequencies of the plurality of field generators, and the digital signal generated by the control circuit is indicative of the frequency components of the voltage drop.

In an embodiment, the control circuit is adapted to generate the digital output signal indicative of an amplitude of the voltage drop and a phase of the voltage drop, and wherein the signal receiver is adapted to determine the coordinates and an orientation of the object, responsive to the amplitude and the phase of the voltage drop indicated by the digital output signal.

In an embodiment, the power storage device includes a capacitor. For some applications, the capacitor has a capacitance between about 5 and 20 microfarads.

In an embodiment, the object includes an implant, and wherein the transponder is fixed in the implant so as to enable the signal receiver to determine the coordinates of the implant within the body.

For example, the apparatus may be configured such that:
the implant includes a joint implant, including a first joint portion and a second joint portion for articulation therewith,
the transponder includes a plurality of transponders fixed respectively to the first joint portion and the second joint portion, and
the signal receiver is adapted to determine a distance between the first joint portion and the second joint portion responsive to the output signal from the transponders.

In an application, the first joint portion includes a femur head and wherein the second joint portion includes an acetabulum.

There is also provided, in accordance with an embodiment of the present invention, a wireless position transponder for operation inside a body of a subject, the transponder including:
  at least one sensor coil, coupled so that a voltage drop across the at least one sensor coil is induced responsive to one or more electromagnetic fields applied to the body in a vicinity of the transponder;
  an arithmetical logic unit (ALU), coupled to the at least one sensor coil so as to generate a digital output signal indicative of the voltage drop across the at least one sensor coil, such that the digital output signal is indicative of coordinates of the transponder inside the body; and
  a power coil, adapted to receive a radio frequency (RF) driving field applied to the body in the vicinity of the transponder, and coupled to convey electrical energy derived from the driving field to the ALU, and further coupled to transmit the digital output signal generated by the ALU so that the signal can be received by processing circuitry outside the body for use in determining the coordinates.

In an embodiment, the transponder includes a power storage device, adapted to store the electrical energy conveyed by the power coil, and to convey the stored electrical energy to the ALU. In this case, the ALU is typically adapted to use the electrical energy conveyed thereto by the power storage device to power the generation of the digital output signal and to power the transmission of the digital output signal.

For some applications, the power storage device includes a capacitor.

The ALU is typically adapted to generate the digital output signal to be indicative of an amplitude and/or a phase of the voltage drop across the at least one sensor coil.

The present invention will be more fully understood from the following detailed description of the embodiments thereof, taken together with the drawings, in which:

DETAILED DESCRIPTION OF EMBODIMENTS

Figure 1:
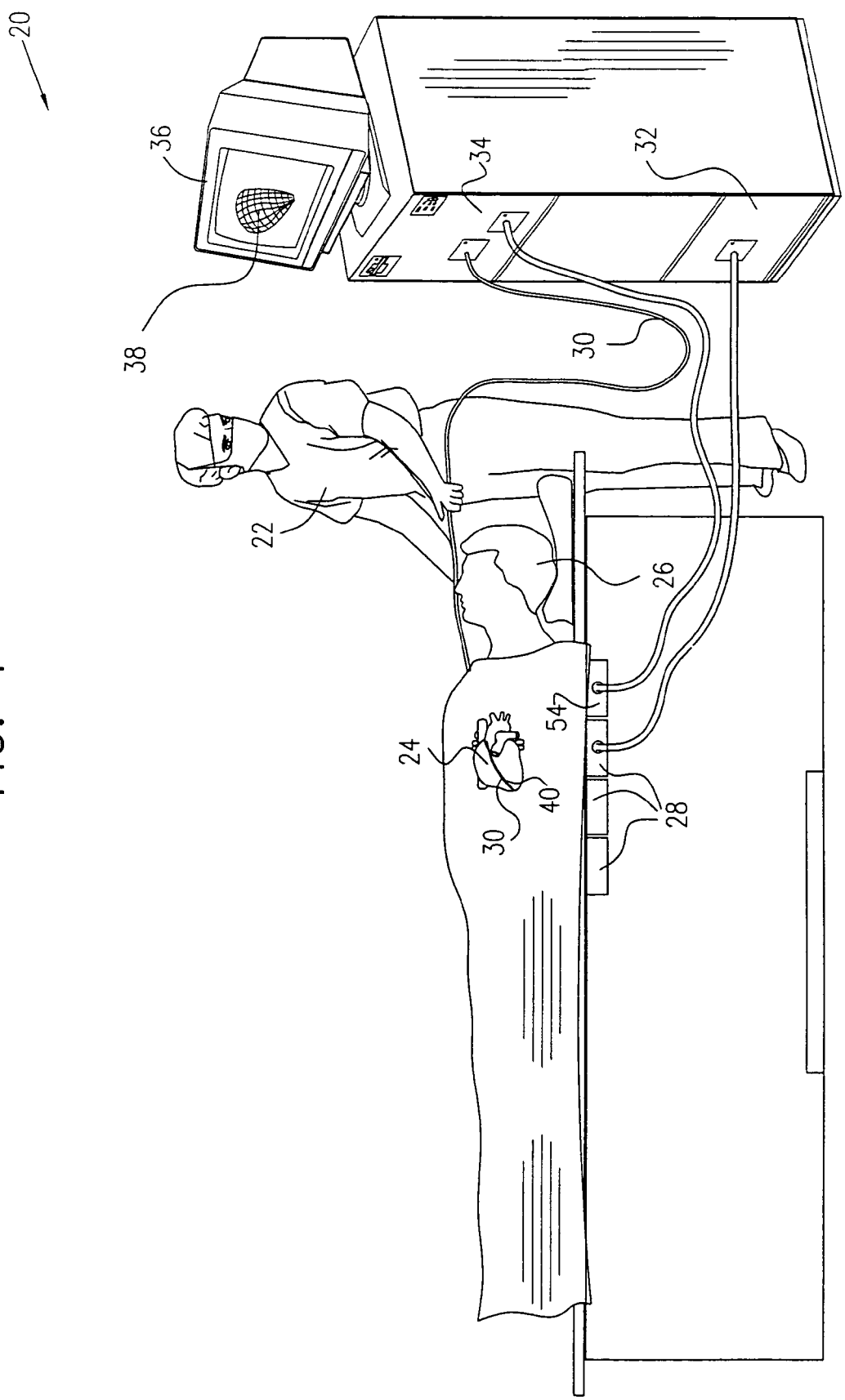
FIG. 1 is a schematic, pictorial illustration of a system for tracking the position of a catheter in the heart, in accordance with an embodiment of the present invention.

FIG. 1 is a schematic, pictorial illustration of a mapping system 20, for mapping a heart 24 of a patient 26, in accordance with an embodiment of the present invention. System 20 comprises an elongate probe, such as a catheter 30, which is inserted by a user 22 through a vein or artery of the patient into a chamber of the heart. Catheter 30 comprises a wireless position transponder 40, typically near the distal tip of the catheter. Transponder 40 is shown in detail in FIG. 2. Optionally, catheter 30 comprises two or more transponders of this sort, mutually spaced along the length of the catheter, in order to give position and orientation coordinates at multiple points along the catheter.

To operate transponder 40, patient 26 is placed in a magnetic field generated, for example, by situating under the patient a pad containing field generator coils 28 for generating a magnetic field. Coils 28 are driven by driver circuits 32 to generate electromagnetic fields, typically at different, respective frequencies. A reference electromagnetic sensor (not shown) is typically fixed relative to the patient, for example, taped to the patient's back, and catheter 30 containing transponder 40 is advanced into the patient's heart. An additional antenna 54, typically in the form of a coil, provides RF power to transponder 40 and receives signals therefrom, as described in detail hereinbelow. Signals received by antenna 54 from transponder 40 in the heart are conveyed to a console 34, which processes the signals and then displays the results on a monitor 36. By this method, the precise location of transponder 40 in catheter 30, relative to the reference sensor, can be ascertained and visually displayed. The transponder can also detect displacement of the catheter that is caused by contraction of the heart muscle.

Some of the features of system 20 are implemented in the above-mentioned CARTO system, including the use of the system to generate a map 38 of cardiac electrical and mechanical function. Further aspects of the design of catheter 30 and of system 20 generally are described in the above-mentioned U.S. Pat. Nos. 5,391,199, 5,443,489 and 6,198,963 and in U.S. Patent Application Publication 2003/0120150. The design of transponder 40 and the associated driver and signal processing circuits used in console 34, however, as described hereinbelow, are unique to the present invention.

Figure 2:
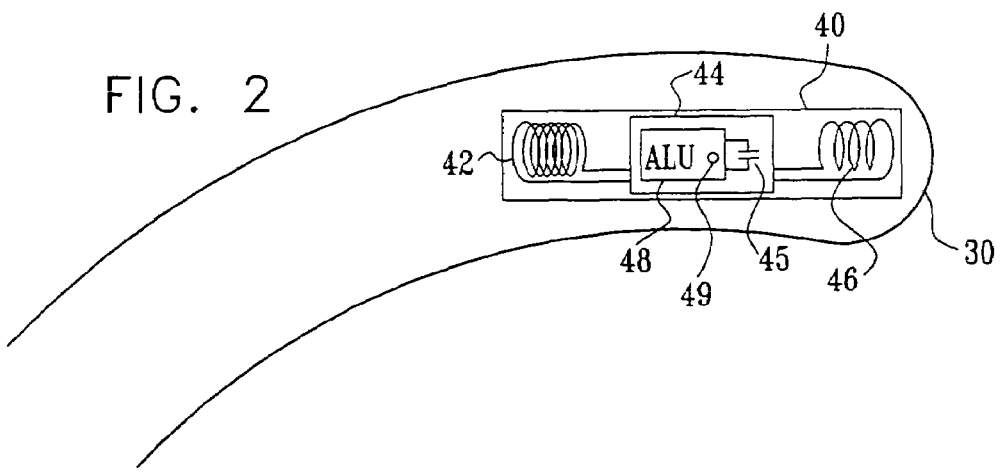
FIG. 2 is a schematic side view of a catheter, showing details of a wireless location transponder in the catheter, in accordance with an embodiment of the present invention.
Figure 3:
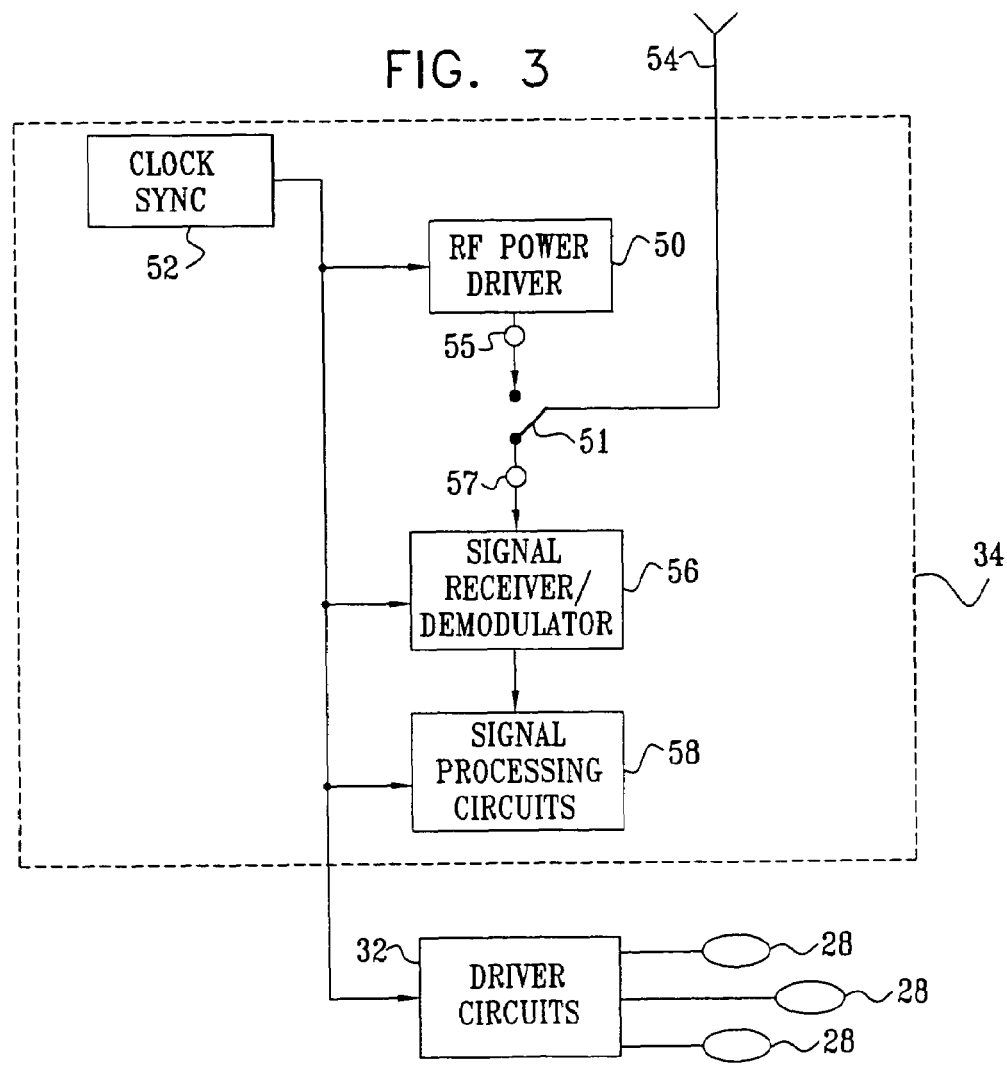
FIG. 3 is a block diagram that schematically illustrates elements of driver and processing circuitry used in a wireless position sensing system, in accordance with an embodiment of the present invention.

Reference is now made to FIGS. 2 and 3, which schematically show details of transponder 40 and of driving and processing circuits in console 34, in accordance with an embodiment of the present invention. As shown in FIG. 2, transponder 40 comprises a power coil 42 and at least one sensing coil 46, coupled to a signal processing chip module 44. Signal processing chip module 44 typically comprises an arithmetical logic unit (ALU) 48 and a power storage device, such as a capacitor 45, typically having a capacitance of about 1 microfarad. Alternatively, the power storage device comprises a battery or other power storage means known in the art. Power coil 42 is typically optimized to receive and transmit high-frequency signals in the range above 1 MHz, e.g., about 13 MHz receiving and about 433 MHz transmitting. Sensing coil 46, on the other hand, is typically designed for operation in the range of 1-3 kHz, the frequencies at which field generator coils 28 generate their electromagnetic fields. Alternatively, other frequency ranges may be used, as dictated by application requirements. The entire transponder 40 is typically 2-5 mm in length and 2-3 mm in outer diameter, enabling it to fit conveniently inside catheter 30.

As shown in FIG. 3, console 34 comprises an RF power driver 50, which drives antenna 54 to emit a power signal, typically in the megahertz range, e.g., about 13 MHz. An optional switch 51, embodied in hardware or software, couples power driver 50 to antenna 54 for the duration of the emission of the power signal. The power signal causes a current to flow in power coil 42 of transponder 40, which current is rectified by signal processing chip module 44 and used to charge capacitor 45. Typically, but not necessarily, console 34 includes a clock synchronization circuit 52, which is used to synchronize RF power driver 50 and driver circuits 32. As mentioned hereinabove, driver circuits 32 drive field generator coils 28 to generate electromagnetic fields. The electromagnetic fields cause a time-varying voltage drop across sensor coil 46 of transponder 40. This voltage drop has frequency components at the same frequencies as the driving currents flowing through the generator coils. The components are proportional to the strengths of the components of the respective magnetic fields produced by the generator coils in a direction parallel to the sensor coil axis. Thus, the voltage drop indicates the position and orientation of coil 46 relative to fixed generator coils 28.

Processing chip module 44 measures the voltage drop across sensor coil 46 at the different field frequencies and, employing ALU 48, digitally encodes the phase and amplitude values of the voltage drop. For some applications, the measured phase and amplitude for each frequency are encoded into a 32-bit value, for example with 16 bits representing phase and 16 bits representing amplitude. Inclusion of phase information in the digital signal allows the resolution of the ambiguity that would otherwise occur in the signals with a 180 degree reversal of the sensing coil axis. The encoded digital values of phase and amplitude are typically stored in a memory 49 in processing chip module 44 using power supplied by capacitor 45. The stored digital values are subsequently transmitted from transponder 40 to console 34 using a digital RF signal, as described hereinbelow with reference to FIG. 4. For some applications, processing chip module 44 digitally encodes and transmits only amplitude values of the voltage drop, and not phase values.

The digitally modulated RF signal is picked up by a receiver 56, which is coupled to antenna 54 via hardware-embodied or software-embodied switch 51. (FIG. 3 shows switch 51 in a state that couples receiver 56 to antenna 54. The receiver demodulates the signal to generate a suitable input to signal processing circuits 58 in console 34. The digital signals are received and used by processing circuits 58 to compute the position and orientation of catheter 30. Typically, circuits 58 comprise a general-purpose computer, which is programmed and equipped with appropriate input circuitry for processing the signals from receiver 56. The information derived by circuits 58 is used to generate map 38, for example, or to provide other diagnostic information or guidance to operator 22.

In an embodiment, console 34 comprises two optional band pass filters 55 and 57, in addition to or instead of switch 51. Band pass filter 55 couples RF power driver 50 to antenna 54, and, for example, may allow energy in a narrow band surrounding 13 MHz to pass to the antenna. Band pass filter 57 couples receiver 56 to antenna 54, and, for example, may allow energy in a narrow band surrounding 433 MHz to pass from the antenna to the receiver. Thus, even in embodiments in which switch 51 is replaced by a T-junction, RF power generated by RF power driver 50 is passed essentially in its entirety to antenna 54, and substantially does not enter circuitry of receiver 56.

The single sensor coil 46 shown in FIG. 2 is sufficient, in conjunction with field generator coils 28, to enable processing circuits 58 to generate three dimensions of position and two dimensions of orientation information. The third dimension of orientation (typically rotation of catheter 30 about its longitudinal axis) can be inferred if needed from mechanical information about the catheter, or, when two or more transponders are used in the catheter, from a comparison of their respective coordinates. Alternatively, transponder 40 may comprise multiple sensor coils, typically three mutually-orthogonal coils, as described, for example, in the above-mentioned European Patent EP 0 776 176. In this case, processing circuits can determine all six position and orientation coordinates of catheter 30 unambiguously.

Figure 4:
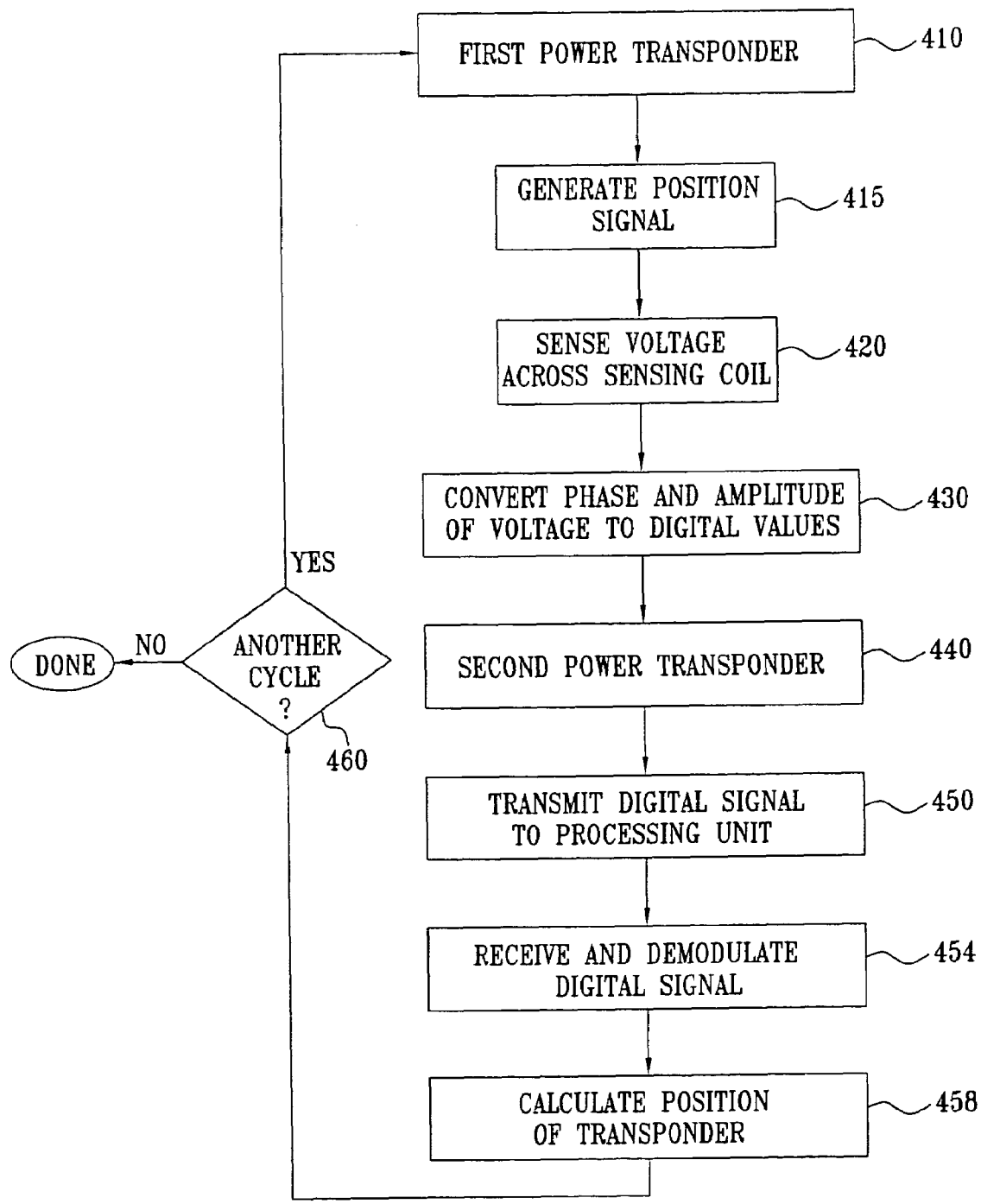
FIG. 4 is a flow chart that schematically illustrates a method for transmitting a digital signal using the system of FIG. 1, in accordance with an embodiment of the present invention.

Reference is now made to FIG. 4, which is a flow chart that schematically illustrates a method for transmitting a digital signal using system 20, in accordance with an embodiment of the present invention. It is emphasized that the particular sequence shown in FIG. 4 is by way of illustration and not limitation, and the scope of the present invention includes other protocols that would be obvious to a person of ordinary skill in the art who has read the disclosure of the present patent application. At a first power transponder step 410, RF power driver 50 generates an RF power signal, typically for about 5 milliseconds, which causes a current to flow in power coil 42, thereby charging capacitor 45. Subsequently, driver circuits 32 drive field generator coils 28 to produce electromagnetic fields, typically for about 20 milliseconds, at a generate position signals step 415. These fields induce a voltage drop across sensor coil 46 of transponder 40, which is measured by signal processing chip module 44, at a sense voltage step 420. Using the power stored in capacitor 45, ALU 48 converts the amplitude and phase of the sensed voltage into digital values, and stores these values in memory 49, at a digital conversion step 430.

If capacitor 45 is constructed such that at this stage it has largely been discharged, then RF power driver 50 again generates an RF power signal, typically for about 5 milliseconds, to recharge capacitor 45, at a second power transponder step 440. Using this stored energy, signal processing chip module 44 generates a digitally-modulated signal based on the stored digital values, and RF-modulates the signal for transmission by power coil 42, at a transmit digital signal step 450. Alternatively, the signal is transmitted using sensing coil 46, for example if a lower frequency is used. This transmission typically requires no more than about 3 milliseconds. Any suitable method of digital encoding and modulation may be used for this purpose, and will be apparent to those skilled in the art, having read the disclosure of the present patent application. Receiver 56 receives and demodulates the digitally-modulated signal, at a receipt and demodulation step 454. Processing circuits 58 use the demodulated signal to compute the position and orientation of transponder 40, at a position calculation step 458.

A check is then performed to determine whether another operation cycle of transponder 40 is to be performed, at a program checking step 460. If no additional cycle is to be performed, the method concludes. If another operation cycle is to be performed, steps 410 through 460 are repeated. Typically, steps 410 through 460 are repeated continuously during use of transponder 40 to allow position and orientation coordinates to be determined in real time.

Figure 5:
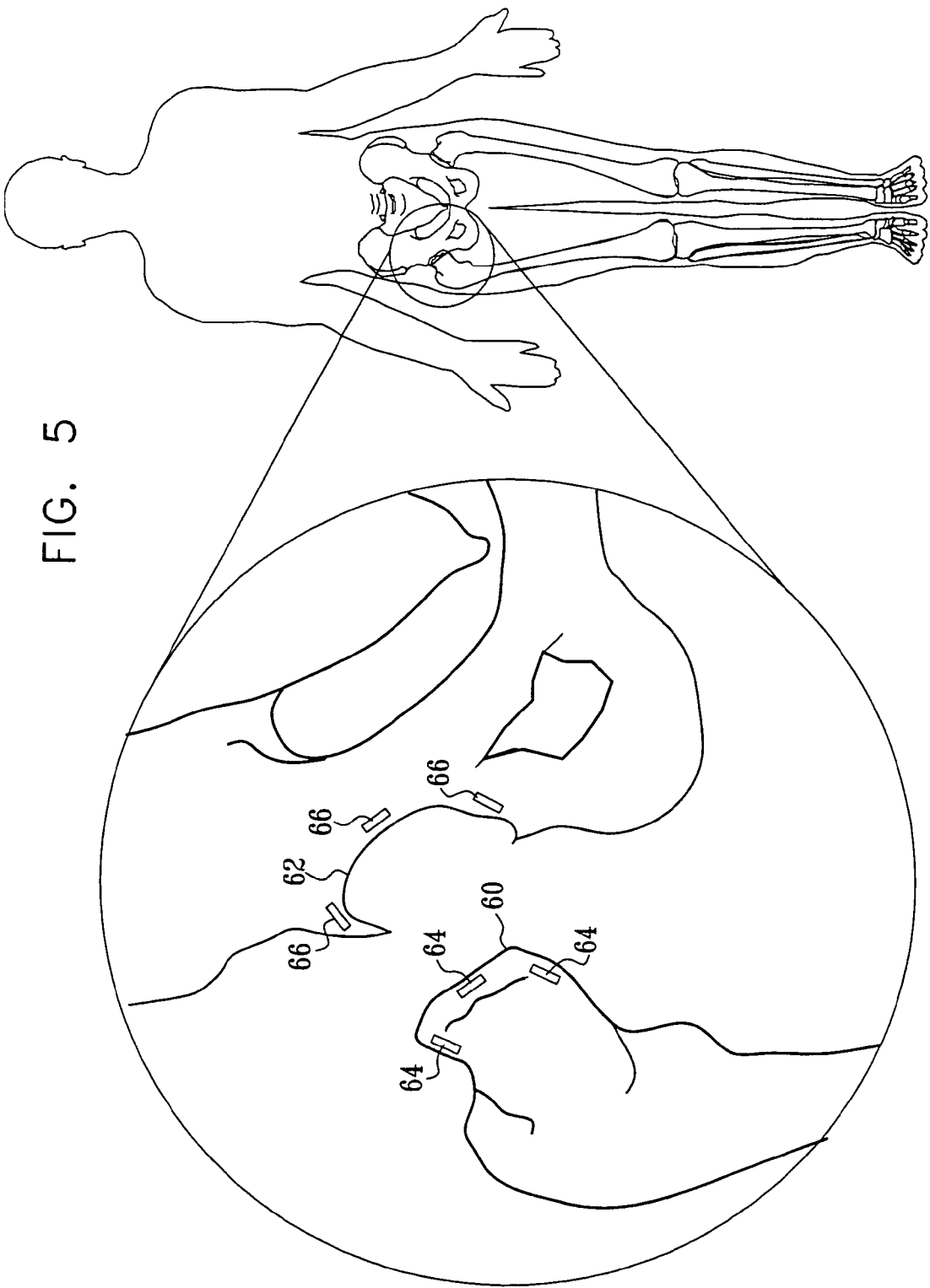
FIG. 5 is a schematic, pictorial illustration showing the use of wireless location transponders in a joint implant, in accordance with an embodiment of the present invention.

FIG. 5 is a schematic, pictorial illustration showing the use of location transponders in an orthopedic procedure, in accordance with an embodiment of the present invention. The use of wireless transponders, such as transponder 40, with a wireless power source, allows the transponders to be inserted in or attached to implantable devices, and then left inside the patient's body for later reference. The embodiment shown in FIG. 5 illustrates hip implant surgery, in which a surgeon is required to position the head of an artificial femur 60 in an artificial acetabulum 62. Typically, before performing the procedure, the surgeon takes X-rays or CT images to visualize the area of the operation, but then performs the actual surgery without the benefit of real-time three-dimensional visualization.

In the embodiment shown in FIG. 5, miniature transponders 64 are embedded in femur 60, and further miniature transponders 66 are embedded in the pelvis in the area of acetabulum 62. Transponders 64 and 66 are typically similar to transponder 40, as shown in FIG. 2. Typically, each transponder is configured to transmit signals back to antenna 54 at a different carrier frequency, so that receiver 56 can differentiate between the transponders. At the beginning of surgery, an X-ray image is taken with the head of the femur in proximity to the acetabulum. The image is captured by computer and displayed on a computer monitor. Transponders 64 and 66 are visible in the X-ray image, and their positions in the image are registered with their respective location coordinates, as determined by processing circuitry 58. During the surgery, the movement of the transponders is tracked by circuitry 58, and this movement is used to update the relative positions of the femur and acetabulum in the image on the monitor, using image processing techniques known in the art. The surgeon uses the updated image to achieve proper placement of the femur head in the acetabulum, without the need for repeated X-ray exposures while the surgery is in process.

After the surgery is finished, the relative positions of transponders 64 and 66 (which remain in the implant) are typically checked periodically to verify that the proper relation is maintained between the bones. This sort of position monitoring is useful both during recovery and for monitoring the status of the implant over the long term. For example, such monitoring may be used to detect increasing separation of the femur from the acetabulum, which is known in some cases to precede more serious bone deterioration.

The techniques described herein enable the determination of the position and orientation of an object in the body without the need for any wired connection between the sensing coil and the external processing unit. Because the power transmission and digital signal transmission do not occur simultaneously, the techniques described herein typically prevent interference between the power transmission signal and the position signal. This lack of interference typically enhances the signal-to-noise ratio. Additionally, only a small amount of digital information is necessary to characterize the voltage generated across the sensing coil. As a result, the transponder requires low power to transmit this digital information, allowing for the use of a small power storage device, such as a capacitor, that can quickly be adequately charged. Furthermore, position coordinates are generally highly accurate because the information is transmitted digitally, and therefore is less susceptible to errors incurred from interference, distortion, or other phenomena sometimes associated with analog signal transmissions.

While FIGS. 1 and 5 show only two particular applications of wireless position transponders in accordance with embodiments of the present invention, other applications will be apparent to those skilled in the art and are considered to be within the scope of the present invention. For example, and not by way of limitation, such transponders may be fixed to other types of invasive tools, such as endoscopes and feeding tubes, as well as to other implantable devices, such as orthopedic implants used in the knee, the spine, and other locations.

In an embodiment of the present invention, a wireless position transponder similar to transponder 40 is provided, which outputs an analog signal instead of a digital signal. A power storage device such as capacitor 45 is used in this embodiment to store energy received by power coil 42. During a time period following reception of the energy by power coil 42, the transponder uses the stored energy to transmit an analog signal whose amplitude and phase are indicative of the position and orientation of sensor coil 46. Typically, techniques described in the above-referenced U.S. Patent Application Publication 2003/0120150 are adapted for use with this embodiment, mutatis mutandis.

It will thus be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for tracking an object, comprising:
   positioning a radio frequency (RF) driver to radiate an RF driving field toward the object;
   fixing to the object a wireless transponder comprising a power coil and at least one sensor coil;
   receiving the RF driving field using the power coil and storing electrical energy derived therefrom;
   driving a plurality of field generators to generate electromagnetic fields at respective frequencies in a vicinity of the object that induce a voltage drop across the at least one sensor coil;
   generating a digital output signal at the wireless transponder indicative of the voltage drop across the sensor coil, and powering the generation of the digital output signal using the stored electrical energy;
   transmitting the digital output signal from the wireless transponder using the power coil, and powering the transmission of the digital output signal using the stored electrical energy; and
   receiving and processing the digital output signal to determine coordinates of the object;
   wherein receiving the RF driving field comprises receiving the RF driving field:
   (a) during a first time period, prior to driving the plurality of field generators, and
   (b) during a second time period, subsequent to the first time period and prior to transmitting the digital output signal,
   wherein storing the electrical energy derived from the RF driving field comprises storing a first electrical energy during the first time period and storing a second electrical energy during the second time period,
   wherein powering the generation of the digital output signal comprises powering the generation of the digital output signal using the first stored electrical energy, and
   wherein powering the transmission of the digital output signal comprises powering the generation of the digital output signal using the second stored electrical energy.

2. A method according to claim 1, wherein driving the plurality of field generators comprises driving the plurality of field generators to generate the electromagnetic fields at different respective frequencies, and wherein the voltage drop across the at least one sensor coil has frequency components at the different respective frequencies of the plurality of field generators.

3. A method according to claim 1, comprising inserting the transponder, together with the object, into a body of a subject, wherein positioning the plurality of field generators and the RF driver comprises placing the plurality of field generators and the RF driver outside the body.

4. A method according to claim 1, comprising inserting the transponder, together with the object, into a body of a subject during a medical procedure, and removing the transponder from the body of the subject during the medical procedure.

5. A method according to claim 1, wherein the object includes an elongate probe, for insertion into a body of a subject, and wherein fixing the transponder to the object comprises fixing the transponder in the probe, and wherein receiving and processing the digital output signal comprises determining the coordinates of a distal end of the probe in the body.

6. A method according to claim 1, wherein generating the digital output signal comprises operating the transponder powered solely by the electrical energy derived from the RF driving field by the power coil.

7. A method according to claim 1, wherein generating the output signal comprises: measuring signal components of the voltage drop; and converting the components into digital values.

8. A method according to claim 7, wherein measuring the signal components comprises measuring an amplitude and a phase.

9. A method according to claim 1, wherein the object includes an implant for implantation in a body of a subject, wherein fixing the transponder to the object comprises fixing the transponder to the implant, and wherein receiving and processing the digital output signal comprises determining the coordinates of the implant within the body.

10. A method according to claim 9, wherein the implant includes a joint implant, including a first joint portion and a second joint portion that articulates therewith,
    wherein fixing the transponder comprises fixing a plurality of transponders respectively to the first joint portion and the second joint portion, and
    wherein determining the coordinates of the implant comprises determining a distance between the first joint portion and the second joint portion responsive to digital output signals from the transponders.

11. A method according to claim 10, wherein determining the distance comprises finding the distance using the transponders during both intraoperative and post-operative periods.

12. A method for tracking an object, comprising:
    radiating a radio frequency (RF) driving field toward the object; receiving the RF driving field at the object, and storing electrical energy derived therefrom;
    subsequently to storing the electrical energy, generating a plurality of electromagnetic fields at respective frequencies in a vicinity of the object;
    using the stored electrical energy, generating a digital output signal indicative of respective strengths of the electromagnetic fields at the object;
    transmitting the digital output signal from the object; and
    receiving and processing the digital output signal to determine coordinates of the object;
    wherein receiving the RF driving field comprises receiving the RF driving field:
    (a) during a first time period, prior to generating the plurality of electromagnetic fields, and
    (b) during a second time period, subsequent to the first time period and prior to transmitting the digital output signal,
    wherein storing the electrical energy derived from the RF driving field comprises storing a first electrical energy during the first time period and storing a second electrical energy during the second time period, wherein generating the digital output signal comprises generating the digital output signal using the first stored electrical energy, and wherein transmitting the digital output signal comprises transmitting the digital output signal using the second stored electrical energy.

13. A method according to claim 12, wherein generating the digital output signal comprises generating the digital output signal solely using the stored electrical energy derived from the RF driving field.

14. A method for tracking an object, comprising:
radiating a radio frequency (RF) driving field toward the object;
receiving the RF driving field at the object, and storing electrical energy derived therefrom;
subsequently to storing the electrical energy, generating a plurality of electromagnetic fields at respective frequencies in a vicinity of the object; using the stored electrical energy, generating an output signal indicative of respective strengths of the electromagnetic fields at the object;
transmitting an output signal from the object; and receiving and processing the output signal to determine coordinates of the object;
wherein receiving the RF driving field comprises receiving the RF driving field:
(a) during a first time period, prior to generating the plurality of electromagnetic fields, and
(b) during a second time period, subsequent to the first time period and prior to transmitting the digital output signal, wherein storing the electrical energy derived from the RF driving field comprises storing a first electrical energy during the first time period and storing a second electrical energy during the second time period, wherein generating the digital output signal comprises generating the digital output signal using the first stored electrical energy, and wherein transmitting the digital output signal comprises transmitting the digital output signal using the second stored electrical energy.

15. A method according to claim 14, wherein generating the output signal comprises generating an analog output signal.

16. Apparatus for tracking an object, comprising:
(a) a radio frequency (RF) driver, adapted to radiate an RF driving field toward the object;
(b) a plurality of field generators, adapted to generate electromagnetic fields at respective frequencies in a vicinity of the object;
(c) a wireless digital transponder, fixed to the object, the transponder comprising:
a power coil, coupled to receive the RF driving field;
a power storage device, adapted to store electrical energy derived from the RF driving field;
at least one sensor coil, coupled so that a voltage drop is induced across the at least one sensor coil responsive to the electromagnetic fields; and
a control circuit, coupled to the at least one sensor coil and to the power storage device, and adapted to use the stored electrical energy to generate a digital output signal indicative of the voltage drop and adapted to use the stored electrical energy to drive the power coil to transmit the digital output signal; and
(d) a signal receiver, adapted to receive the digital output signal transmitted by the power coil and, responsive thereto, to determine coordinates of the object;
wherein the power storage device is adapted to store a first electrical energy derived from the RF driving field during a first time period,
wherein the control circuit is adapted to use the first stored electrical energy to generate the digital output signal,
wherein the power storage device is adapted to store second electrical energy derived from the RF driving field during a second time period, following the first time period and following the generating by the control circuit of the digital output signal, and
wherein the control circuit is adapted to use the second stored electrical energy to drive the power coil to transmit the digital output signal.

17. Apparatus according to claim 16, wherein the plurality of field generators are adapted to generate the electromagnetic fields at different respective frequencies.

18. Apparatus according to claim 16, wherein the control circuit is adapted to operate powered solely by the electrical energy conveyed thereto by the power coil.

19. Apparatus according to claim 16, wherein the voltage drop across the at least one sensor coil has frequency components at the different frequencies of the plurality of field generators, and wherein the digital signal generated by the control circuit is indicative of the frequency components of the voltage drop.

20. Apparatus according to claim 16, wherein the control circuit is adapted to generate the digital output signal indicative of an amplitude of the voltage drop and a phase of the voltage drop, and wherein the signal receiver is adapted to determine the coordinates and an orientation of the object, responsive to the amplitude and the phase of the voltage drop indicated by the digital output signal.

21. Apparatus according to claim 16, wherein the power storage device comprises a capacitor.

22. Apparatus according to claim 21, wherein the capacitor has a capacitance between about 5 and 20 microfarads.

23. Apparatus according to claim 16, wherein the object comprises an implant, and wherein the transponder is fixed in the implant so as to enable the signal receiver to determine the coordinates of the implant within the body.

24. Apparatus according to claim 23, wherein the implant comprises a joint implant, comprising a first joint portion and a second joint portion for articulation therewith,
wherein the transponder comprises a plurality of transponders fixed respectively to the first joint portion and the second joint portion, and
wherein the signal receiver is adapted to determine a distance between the first joint portion and the second joint portion responsive to the output signal from the transponders.

25. Apparatus according to claim 24, wherein the first joint portion comprises a femur head and
wherein the second joint portion comprises an acetabulum.

26. A wireless position transponder for operation inside a body of a subject, the transponder comprising:
at least one sensor coil, coupled so that a voltage drop across the at least one sensor coil is induced responsive to one or more electromagnetic fields applied to the body in a vicinity of the transponder;
an arithmetical logic unit (ALU), coupled to the at least one sensor coil so as to generate a digital output signal indicative of the voltage drop across the at least one sensor coil, such that the digital output signal is indicative of coordinates of the transponder inside the body;
a power coil, adapted to receive a radio frequency (RF) driving field applied to the body in the vicinity of the transponder, and coupled to convey electrical energy derived from the driving field to the ALU, and further coupled to transmit the digital output signal generated by the ALU so that the signal can be received by processing circuitry outside the body for use in determining the coordinates; and
a power storage device, adapted to store the electrical energy conveyed by the power coil, and to convey the stored electrical energy to the ALU,
wherein the ALU is adapted to use the electrical energy conveyed thereto by the power storage device to power the generation of the digital output signal and to power the transmission of the digital output signal;

wherein the power storage device is adapted to store first electrical energy derived from the RF driving field during a first time period, wherein the control circuit is adapted to use the first stored electrical energy to generate the digital output signal, wherein the power storage device is adapted to store second electrical energy derived from the RF driving field during a second time period, following the first time period and following the generating by the control circuit of the digital output signal, and wherein the control circuit is adapted to use the second stored electrical energy to drive the power coil to transmit the digital output signal.

27. A transponder according to claim 26, wherein the power storage device comprises a capacitor.

28. A transponder according to claim 26, wherein the ALU is adapted to generate the digital output signal to be indicative of an amplitude and a phase of the voltage drop across the at least one sensor coil.

29. A transponder according to claim 26, wherein the power coil is adapted to receive and transmit signals within a first range of frequencies; and the sensor coil is adapted to operate within a second range of frequencies; the first range of frequencies of the power coil being higher than the second range of frequencies of the sensor coil.

30. A transponder according to claim 29, wherein the first range of frequencies of the power coil is above 1 MHz.

31. A transponder according to claim 29, wherein the second range of frequencies of the sensor coil is between 1-3 kHz.

* * * * *